US012766037B2

(12) United States Patent
Zheleznyak et al.

(10) Patent No.: US 12,766,037 B2
(45) Date of Patent: Oct. 20, 2026

(54) LIRIC CALIBRATION BASED ON MULTIPHOTON EXCITATION

(71) Applicant: Clerio Vision, Inc., Rochester, NY (US)

(72) Inventors: Leonard Zheleznyak, Pittsford, NY (US); Sam Butler, Rochester, NY (US); Steven Cox, Rochester, NY (US); Aaron Michalko, Rochester, NY (US)

(73) Assignee: Clerio Vision, Inc., Rochester, NY (US)

( * ) Notice: Subject to any disclaimer, the term of this patent is extended or adjusted under 35 U.S.C. 154(b) by 403 days.

(21) Appl. No.: 18/212,833

(22) Filed: Jun. 22, 2023

(65) Prior Publication Data

US 2023/0329910 A1 Oct. 19, 2023

Related U.S. Application Data

(63) Continuation of application No. PCT/US2021/064147, filed on Dec. 17, 2021.

(Continued)

(51) Int. Cl.

*A61F 9/008* (2006.01)
*A61B 17/00* (2006.01)

(52) U.S. Cl.

CPC .... *A61F 9/008* (2013.01); *A61B 2017/00181* (2013.01); *A61F 2009/00844* (2013.01);

(Continued)

(58) Field of Classification Search

CPC ............ A61F 9/008; A61F 2009/00844; A61F 2009/00855; A61F 2009/0087; A61F 2009/00897; A61B 2017/00181

(Continued)

(56) References Cited

U.S. PATENT DOCUMENTS 7,789,910 B2 9/2010 Knox et al.
8,337,553 B2 12/2012 Knox et al.

(Continued)

FOREIGN PATENT DOCUMENTS

WO 9316631 A1 9/1993
WO 2008002796 A2 1/2008

(Continued)

OTHER PUBLICATIONS

Flitcroft et al., "IMI—Defining and Classifying Myopia: A Proposed Set of Standards for Clinical and Epidemiologic Studies", Investigative Ophthalmology & Visual Science, vol. 60, No. 3, Feb. 2019, pp. M20-M30.

(Continued)

*Primary Examiner* — Ahmed M Farah
(74) *Attorney, Agent, or Firm* — Kilpatrick Townsend & Stockton LLP

(57) ABSTRACT

Calibration of laser pulse powers used to form subsurface optical structures in an ophthalmic lens is accomplished via generation of a feedback signal indicative of pulse energy absorption. A system for forming subsurface optical structures within an ophthalmic lens includes a laser pulse source, a laser pulse power control assembly, a scanning assembly, a detector, and a control unit. The laser pulse power control assembly is operable to selectively control an energy of respective laser pulses. The detector is configured to generate a feedback signal indicative of an energy absorbed by the ophthalmic lens from a first laser pulse. The control unit is configured to control operation of the laser pulse power control assembly to selectively control an energy of a second laser pulse based on a selected energy of the second laser pulse, a selected energy of the first laser pulse, and the feedback signal.

20 Claims, 7 Drawing Sheets

Related U.S. Application Data

(60) Provisional application No. 63/129,023, filed on Dec. 22, 2020.

(52) U.S. Cl.
CPC ............... *A61F 2009/00855* (2013.01); *A61F 2009/0087* (2013.01); *A61F 2009/00897* (2013.01)

(58) Field of Classification Search
USPC ........................................................ 606/5
See application file for complete search history.

(56) References Cited

U.S. PATENT DOCUMENTS

| | | | | |
|---|---|---|---|---|
| 8,512,320 | B1 | 8/2013 | Knox et al. | |
| 8,617,147 | B2 | 12/2013 | Knox et al. | |
| 8,901,190 | B2 | 12/2014 | Smith et al. | |
| 8,932,352 | B2 | 1/2015 | Knox et al. | |
| 9,060,847 | B2 | 6/2015 | Smith et al. | |
| 9,144,491 | B2 | 9/2015 | Knox et al. | |
| 9,492,323 | B2 | 11/2016 | Knox et al. | |
| 9,545,340 | B1 | 1/2017 | Knox et al. | |
| 9,622,912 | B2 | 4/2017 | Knox et al. | |
| 9,939,558 | B2 | 4/2018 | Knox et al. | |
| 10,226,381 | B2 | 3/2019 | Knox et al. | |
| 11,369,515 | B2 * | 6/2022 | Zheleznyak | A61F 9/00812 |
| 2008/0001320 | A1 | 1/2008 | Knox et al. | |
| 2009/0275929 | A1 | 11/2009 | Zickler | |
| 2012/0310223 | A1 | 12/2012 | Knox et al. | |
| 2012/0310340 | A1 | 12/2012 | Knox et al. | |
| 2013/0178934 | A1 | 7/2013 | Knox et al. | |
| 2013/0226162 | A1 | 8/2013 | Knox et al. | |
| 2015/0100012 | A1 * | 4/2015 | Muller | A61N 5/062 604/20 |
| 2015/0112203 | A1 * | 4/2015 | Bille | A61B 3/0008 600/473 |
| 2015/0133902 | A1 | 5/2015 | Reich et al. | |
| 2015/0378065 | A1 * | 12/2015 | Knox | B29D 11/023 359/652 |
| 2016/0144580 | A1 | 5/2016 | Knox et al. | |
| 2017/0035613 | A1 | 2/2017 | Knox et al. | |
| 2017/0181846 | A1 | 6/2017 | Knox et al. | |
| 2018/0021172 | A1 | 1/2018 | Zheleznyak et al. | |
| 2018/0206979 | A1 | 7/2018 | Knox et al. | |
| 2018/0231696 | A1 | 8/2018 | Knox et al. | |
| 2018/0243082 | A1 | 8/2018 | Zheleznyak et al. | |
| 2018/0373060 | A1 | 12/2018 | Knox et al. | |
| 2019/0046357 | A1 | 2/2019 | Knox et al. | |
| 2019/0343683 | A1 * | 11/2019 | Zheleznyak | A61F 9/00829 |
| 2020/0054485 | A1 | 2/2020 | Knox | |
| 2021/0378508 | A1 * | 12/2021 | Zheleznyak | A61B 3/028 |

FOREIGN PATENT DOCUMENTS

| | | | |
|---|---|---|---|
| WO | 2009143054 | A2 | 11/2009 |
| WO | 2012166696 | A1 | 12/2012 |
| WO | 2015006274 | A1 | 1/2015 |
| WO | 2017106321 | A1 | 6/2017 |
| WO | 2018182946 | A1 | 10/2018 |
| WO | 2019010345 | A1 | 1/2019 |
| WO | 2019147952 | A1 | 8/2019 |
| WO | 2020102514 | A1 | 5/2020 |
| WO | 2021108585 | A1 | 6/2021 |
| WO | 2021202247 | A1 | 10/2021 |

OTHER PUBLICATIONS

Hiraoka et al., “Relationships Between Higher-order Wavefront Aberrations and Natural Progression of Myopia in Schoolchildren”, Scientific Reports, vol. 7, Article No. 7876, Aug. 11, 2017, 9 Pages.
Huang et al., “Efficacy Comparison of 16 Interventions for Myopia Control in Children”, America Academy of Ophthalmology, vol. 123, No. 4, Apr. 2016, pp. 697-708.
Li et al., “Studies Using Concentric Ring Bifocal and Peripheral Add Multifocal Contact Lenses to Slow Myopia Progression in School-Aged Children: A Meta-Analysis”, Ophthalmic & Physiological Optics, vol. 37, No. 1, Jan. 2017, pp. 51-59.
Moreno et al., “Modulation Light Efficiency of Diffractive Lenses Displayed in a Restricted Phase-Mostly Modulation Display”, Applied Optics, vol. 43, No. 34, Dec. 1, 2004, pp. 6278-6284.
Resnikoff et al., “Myopia—A 21st Century Public Health Issue”, Investigative Ophthalmology & Visual Science, vol. 60, No. 3, Feb. 2019, pp. Mi-Mii.
Savage et al., “First Demonstration of Ocular Refractive Change Using Blue-IRIS in Live Cats”, Investigative Ophthalmology & Visual Science, vol. 55, No. 7, Jul. 1, 2014, pp. 4603-4612.
Si et al., “Orthokeratology for Myopia Control: A Meta-Analysis”, Optometry and Vision Science, vol. 92, No. 3, Mar. 2015, pp. 252-257.
Smith et al., “Peripheral Vision Can Influence Eye Growth and Refractive Development in Infant Monkeys”, Investigative Ophthalmology & Visual Science, vol. 46, No. 11, Nov. 2005, 16 Pages.
Tedja et al., “IMI—Myopia Genetics Report”, Investigative Ophthalmology & Visual Science, vol. 60, No. 3, Feb. 2019, pp. M89-M105.
Troilo et al., “IMI—Report on Experimental Models of Emmetropization and Myopia”, Investigative Ophthalmology & Visual Science, vol. 60, No. 3, Feb. 2019, pp. M31-M88.
Wildsoet et al., “IMI—Interventions for Controlling Myopia Onset and Progression Report”, Investigative Ophthalmology & Visual Science, vol. 60, No. 3, Feb. 2019, pp. M106-M131.
Wolffsohn et al., “IMI—Clinical Myopia Control Trials and Instrumentation Report”, Investigative Ophthalmology & Visual Science, vol. 60, No. 3, Feb. 2019, pp. M132-M160.
Wolffsohn et al., “IMI—Myopia Control Reports Overview and Introduction”, Investigative Ophthalmology & Visual Science, vol. 60, No. 3, Feb. 2019, pp. M1-M19.
Xu et al., “Noninvasive Intratissue Refractive Index Shaping (IRIS) of the Cornea with Blue Femtosecond Laser Light”, Investigative Ophthalmology & Visual Science, vol. 52, No. 11, Oct. 17, 2011, pp. 8148-8155.

* cited by examiner

LIRIC CALIBRATION BASED ON MULTIPHOTON EXCITATION

CROSS REFERENCES TO RELATED APPLICATIONS

The present application is a Continuation of PCT/US2021/064147 filed Dec. 17, 2021; which claims priority to U.S. Provisional Appln. No. 63/129,023 filed Dec. 22, 2020; the disclosures which are incorporated herein by reference in their entirety for all purposes.

BACKGROUND

Optical aberrations that degrade visual acuity are common. Optical aberrations are imperfections of the eye that degrade focusing of light onto the retina. Common optical aberrations include lower-order aberrations (e.g., astigmatism, positive defocus (myopia) and negative defocus (hyperopia)) and higher-order aberrations (e.g., spherical aberrations, coma and trefoil).

Existing treatment options for correcting optical aberrations include glasses, contact lenses and reshaping of the cornea via laser eye surgery. Additionally, intraocular lenses are often implanted to replace native lenses removed during cataract surgery.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments described herein are directed to systems and related methods for forming subsurface optical structures within an ophthalmic lens. In many embodiments, a sequence of laser pulses is focused onto a sequence of focal positions within an ophthalmic lens to form subsurface optical structures by inducing subsurface refractive index changes in the ophthalmic lens. The induced refractive index changes (locations and magnitudes) are controlled by controlling the scanning of the focal positions of the sequence of laser pulses and the power of each of the laser pulses. In many embodiments, a detector is used to generate a feedback signal indicative of amount of energy of a laser pulse absorbed by the ophthalmic lens. In many embodiments, the feedback signal is used to calibrate control of the power of each of the laser pulses to more closely produce desired amounts of pulse energy absorption by the ophthalmic lens for the sequence of laser pulses. By employing the feedback signal to more accurately produce desired amounts of pulse energy absorbed, the subsurface optical structures can be formed more accurately despite variations between ophthalmic lenses that impact energy absorption characteristics.

In one aspect, a system for forming subsurface optical structures within an ophthalmic lens includes a laser pulse source, a laser pulse power control assembly, a scanning assembly, a detector, and a control unit. The laser pulse source is operable to generate a sequence of laser pulses. The laser pulse power control assembly is operable to selectively control power of respective laser pulses of the sequence of laser pulses. The scanning assembly is controllable to focus the sequence of laser pulses onto sub-volumes of the ophthalmic lens. The detector is configured to generate a feedback signal indicative of an energy absorbed by the ophthalmic lens from a first laser pulse of the sequence of laser pulses. The control unit is operatively coupled with the laser pulse power control assembly and the detector. The control unit is configured to control operation of the laser pulse power control assembly to selectively control power of a second laser pulse of the sequence of laser pulses based on a selected power of the second laser pulse, a selected power of the first laser pulse and the feedback signal.

In some embodiments of the system, the feedback signal is indicative of a first fluorescence emitted by the ophthalmic lens in response to the energy absorbed by the ophthalmic lens from the first laser pulse. In some embodiments, the system includes one or more optical filters configured to: (a) block a wavelength of light of the first laser pulse from reaching the detector; and (b) transmit wavelengths of light of the first fluorescence so that the wavelengths of light of the first fluorescence reach the detector. In some embodiments, the system includes an integrating sphere configured to diffuse the first fluorescence prior to the first fluorescence reaching the detector. In some embodiments of the system, the first fluorescence propagates back through the scanning assembly prior to reaching the detector. In some embodiments, the system includes a reflector that reflects a portion of the first fluorescence so as to propagate back through the scanning assembly prior to reaching the detector. In some embodiments, the system includes a collimator that collimates the first fluorescence prior to reaching the detector.

In some embodiments of the system, the feedback signal is indicative of an energy of a transmitted portion of the first laser pulse, wherein the transmitted portion of the first laser pulse is not absorbed by the first volume. In some embodiments, the system includes an integrating sphere configured to diffuse the transmitted portion of the first laser pulse prior to the transmitted portion of the first laser pulse reaching the detector. In some embodiments of the system, the transmitted portion of the first laser pulse propagates back through the scanning assembly prior to reaching the detector. In some embodiments, the system includes a reflector that reflects a portion of the transmitted portion of the first laser pulse so as to propagate back through the scanning assembly prior to reaching the detector. In some embodiments, the system includes a collimator that collimates the transmitted portion of the first laser pulse prior to reaching the detector.

The detector can be integrated into the system in any suitable manner. For example, in some embodiments, the system includes one or more positioning stages controlled by the control unit to reposition the detector relative to the ophthalmic lens during formation of the subsurface optical structures within the ophthalmic lens. In some embodiments, the system includes one or more positioning stages controlled by the control unit to reposition the ophthalmic lens and the detector relative to the scanning assembly during formation of the subsurface optical structures within the ophthalmic lens.

The detector can have any suitable configuration for generating the feedback signal. For example, in some embodiments of the system, the detector includes an imaging device configured to image a two-dimensional area sized to accommodate a two-dimensional scanning area over which the sequence of laser pulses are scanned into the ophthalmic lens during formation of the subsurface optical structures within the ophthalmic lens. In some embodiments of the system, the detector comprises a photometer.

The laser pulse power control assembly can have any suitable configuration for selectively controlling power of respective laser pulses of the sequence of laser pulses. For example, in some embodiments of the system, the laser pulse power control assembly includes an acousto-optic modulator.

The system can be used to form subsurface optical structures in any suitable type of ophthalmic lens. For example, in some embodiments of the system, the ophthalmic lens includes a contact lens. In some embodiments of the system, the ophthalmic lens includes an in vivo natural lens of a subject. In some embodiments of the system, the ophthalmic lens comprises an implanted intraocular lens. In some embodiments of the system, the ophthalmic lens includes a cornea of a subject.

In another aspect, a method of calibrating one or more laser pulse power calibration parameters used to determine pulse power for laser pulses from designated energy absorption amounts for the laser pulses is provided. The method includes: (a) generating a laser pulse used to produce a power-adjusted laser pulse, (b) determine an adjusted pulse power for the power-adjusted laser pulse from a designated energy absorption by an ophthalmic lens for the power-adjusted laser pulse based on one or more laser pulse power calibration parameters, (c) adjusting power of the laser pulse to produce the power-adjusted laser pulse, wherein the power-adjusted laser pulse has the adjusted pulse power, (d) focusing the power-adjusted laser pulse onto a sub-volume of the ophthalmic lens, (e) generating a feedback signal, by a detector, indicative of an energy absorbed by the ophthalmic lens from the power-adjusted laser pulse, and (f) updating the one or more calibration parameters based on the feedback signal and the designated energy absorption by the ophthalmic lens for the power-adjusted laser pulse.

In some embodiments of the method, the feedback signal is indicative of a fluorescence emitted by the ophthalmic lens in response to the energy absorbed from the power-adjusted laser pulse. In some embodiments, the method includes: (a) blocking a wavelength of light of the power-adjusted laser pulse from reaching the detector, and (b) transmitting wavelengths of light of the fluorescence so that the wavelengths of light of the fluorescence reach the detector. In some embodiments, the method includes diffusing the fluorescence prior to the fluorescence reaching the detector. In some embodiments, the method includes propagating the fluorescence back through a scanning assembly prior to reaching the detector, wherein the scanning assembly is used to focus the power-adjusted laser pulse onto the sub-volume of the ophthalmic lens. In some embodiments, the method includes reflecting a portion of the fluorescence so as to propagate back through the scanning assembly prior to reaching the detector. In some embodiments, the method includes collimating the fluorescence prior to reaching the detector.

In some embodiments of the method, the feedback signal is indicative of an energy of a transmitted portion of the power-adjusted laser pulse, wherein the transmitted portion of the power-adjusted laser pulse is not absorbed by the ophthalmic lens. In some embodiments, the method includes diffusing the transmitted portion prior to the transmitted portion reaching the detector. In some embodiments, the method includes propagating the transmitted portion back through the scanning assembly prior to reaching the detector. In some embodiments, the method includes reflecting a portion of the transmitted portion so as to propagate back through the scanning assembly prior to reaching the detector. In some embodiments, the method includes collimating the transmitted portion prior to reaching the detector.

In some embodiments of the method, the detector is repositioned during formation of the subsurface optical structures in the ophthalmic lens. For example, in some embodiments, the method includes repositioning the detector relative to the ophthalmic lens in coordination with scanning of a sequence of power-adjusted laser pulses during formation of subsurface optical structures within the ophthalmic lens. In some embodiments, the method includes repositioning the ophthalmic lens and the detector relative to the scanning assembly in coordination with scanning of a sequence of power-adjusted laser pulses during formation of subsurface optical structures within the ophthalmic lens.

Any suitable detector can be used to practice the method. For example, in some embodiments of the method, the detector includes an imaging device configured to image a two-dimensional area sized to accommodate a two-dimensional scanning area over which a sequence of power-adjusted laser pulses are scanned into the ophthalmic lens during formation of subsurface optical structures within the ophthalmic lens. In some embodiments of the method, the detector includes a photometer.

Any suitable approach can be used to adjust power of the laser pulse to produce the power-adjusted laser pulse. For example, adjusting the power of the laser pulse to produce the power-adjusted laser pulse can include transmitting the laser pulse through an acousto-optic modulator.

The method can be used to form subsurface optical structures in any suitable type of ophthalmic lens. For example, in some embodiments of the method, the ophthalmic lens includes a contact lens. In some embodiments of the method, the ophthalmic lens includes an in vivo natural lens of a subject. In some embodiments of the method, the ophthalmic lens comprises an implanted intraocular lens. In some embodiments of the method, the ophthalmic lens includes a cornea of a subject.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
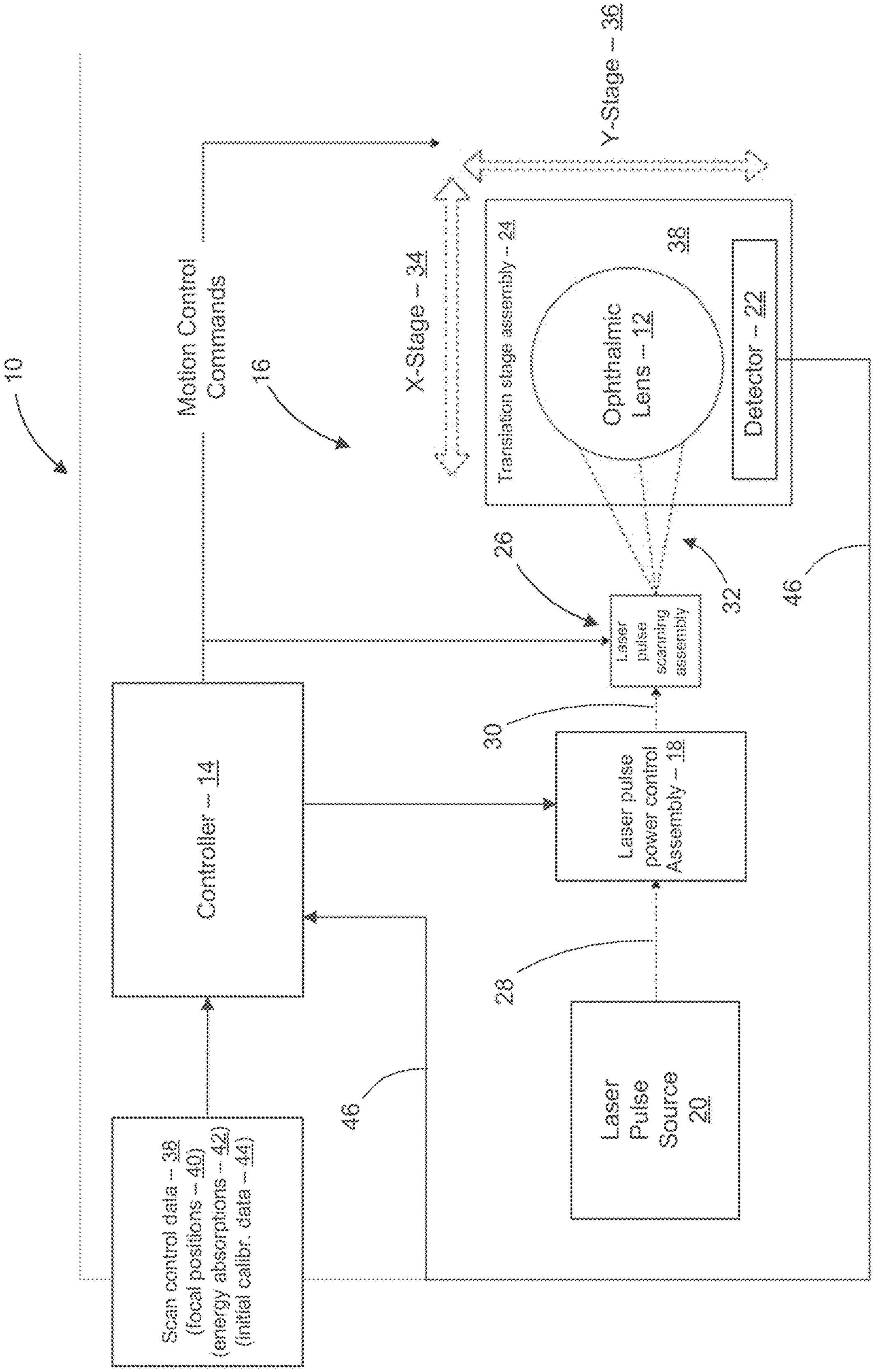
FIG. 1 is a simplified schematic illustration of a system for forming subsurface optical structures within an ophthalmic lens, in accordance with embodiments.

Turning now to the drawing figures, in which like reference numbers refer to like elements in the various figures, FIG. 1 is a simplified schematic illustration of a system 10 for forming subsurface optical structures in an ophthalmic lens 12, in accordance with embodiments. The system 10 includes a controller 14, a scanning assembly 16, a laser pulse power control assembly 18, a laser pulse source 20, and a detector 22. In the illustrated embodiment, the scanning assembly 16 includes a translation stage assembly 24 and a laser pulse scanning assembly 26.

In many embodiments, the laser pulse source 20 is operable to generate a sequence of suitable laser pulses 28 for use forming desired subsurface optical structures in the ophthalmic lens 12. The laser pulses 28 have a suitable wavelength for inducing refractive index changes in the target subvolumes of the ophthalmic lens 12. In some embodiments, the laser pulses 28 have a 1035 nm central wavelength. The laser pulses 28, however, can have any suitable central wavelength (e.g., in a range from 400 to 1100 nm) effective in inducing refractive index changes in the target subvolumes of the ophthalmic lens 12. In many embodiments, the laser pulse source 20 is operable to emit a sequence of the laser pulses 28 at a suitable pulse length (e.g., 5 to 500 fs) at a suitable frequency (e.g., 1 to 80 Mhz) with a suitable pulse power (e.g., for 400 nm regime, kW peak pulse powers, mW average powers).

The laser pulse power control assembly 18 is controllable to selectively vary the power of the laser pulses 28. The laser pulse power control assembly 18 can have any suitable configuration, including any suitable known configuration for selectively controlling the power of the laser pulses 28. For example, in some embodiments, the laser pulse power control assembly 18 includes an acousto-optic modulator (AOM). The AOM can include a piezoelectric transducer that vibrates a material (e.g., glass, quartz) through which the laser pulses 28 travel. The amplitude of vibration can be controllably varied to selectively modulate the power level of the laser pulses 30 emitted from the laser pulse power control assembly 18. The vibration may be varied between any suitable range so as to vary the power level of the emitted laser pulses 30 between a suitable corresponding range. The AOM can be used to adjust the power level of the emitted laser pulses 30 very precisely at small increments in nanosecond time frames. In some embodiments, the laser pulse power control assembly 18 is operable to block transmission of the laser pulses 28 so as to block the laser pulses 28 from reaching the ophthalmic lens 12 for a period of time. Alternatively or additionally, a mechanical means (e.g., a physical shutter disposed somewhere between the laser pulse source 20 and the ophthalmic lens 12) may be used to ensure that the laser pulses 28 do not reach the ophthalmic lens 12 for a period of time.

The laser pulse scanning assembly 26 is controllable to selectively scan the focal position of the power adjusted laser pulses 30 to produce XY scanned laser pulses 32. The laser pulse scanning assembly 26 can have any suitable configuration, including any suitable known configuration to produce the XY scanned laser pulses 32. In many embodiments, the laser pulse scanning assembly 26 is controllable to selectively scan the laser beam pulses 30 in two orthogonal directions transverse to the direction of propagation of the XY scanned laser pulses 32.

The laser pulse scanning assembly 26 can include an XY scanning unit, a relay optical assembly and a scanning/interface assembly. The XY scanning unit can include a dual axis galvo mirror scanning system to controllably redirect the power adjusted laser pulses 30 in orthogonal X and Y directions. The relay optical assembly can receive the XY scanned laser pulses from the XY scanning unit and output the XY scanned laser pulses to the scanning/interface assembly in a manner that minimizes vignetting. The relay optical assembly can have any suitable configuration to relay the XY scanned laser pulses 32 to the scanning/interface assembly.

In the illustrated embodiments, the ophthalmic lens 12 is mounted to the translation stage assembly 24. The translation stage assembly 24 includes a stationary base, a motorized X-stage 34, a motorized Y-stage 36, and a support platform 38. The support platform 38 can have a support fixture configured to support an ophthalmic lens 12 mounted to the support fixture in a fixed position and orientation relative to the support platform 38. The motorized X-stage 34 is controllable by the controller 14 to selectively reposition the support platform 38 in the X-direction relative to the stationary base and thereby selectively reposition the ophthalmic lens 12 in the X-direction relative to the laser pulse scanning assembly 26. Likewise, the motorized Y-stage 36 is controllable by the controller 14 to selectively reposition the support platform 38 in the Y-direction relative to the stationary base and thereby selectively reposition the ophthalmic lens 12 in the Y-direction relative to the laser pulse scanning assembly 26.

In the illustrated embodiments, the controller 14 is configured to accomplish coordinated control of the laser pulse source 20, the laser pulse power control assembly 18, the laser pulse scanning assembly 26, the motorized X-stage 34 and the motorized Y-stage 36 to scan focal positions of laser pulses of selected pulse power within the ophthalmic lens 12 to form desired subsurface optical structures in the ophthalmic lens 12. The controller 14 receives scan control data 38, which defines the focal positions 40 of the sequence of laser pulses within the ophthalmic lens 12, defines desired absorbed pulse energies 42 of the sequence of laser pulses, and includes initial calibration data 44 that defines initial one or more calibration parameters that are initially used to determine the powers of the power adjusted laser pulses 30 from the desired absorbed pulse energies 42.

The detector 22 generates and outputs a feedback signal 46 indicative of energy absorbed by the ophthalmic lens 12 from one or more laser pulses of the sequence of laser pulses. The detector 22 transmits the feedback signal 46 to the controller 14. The controller 14 processes the feedback signal 46 to measure how much energy was absorbed by the ophthalmic lens 12 from the one or more laser pulses of the sequence laser pulses. The controller 14 then compares the measured energy absorption with the predefined desired energy absorption to determine whether to adjust the current calibration relationship between the desired absorbed pulse energies 42 and the powers of the power adjusted laser pulses 30. Where the measured energy absorption is lower than the desired energy absorption, the calibration relationship can be adjusted to increase the magnitude of the ratio of power of the power adjusted laser pulse 30 to the desired absorbed pulse energy 42 for subsequent laser pulses by a suitable ratio. Where the measured energy absorption is higher than the desired energy absorption, the calibration relationship can be adjusted to decrease the magnitude of the ratio of power of the power adjusted laser pulse 30 to the desired absorbed pulse energy 42 for subsequent laser pulses by a suitable ratio. To enhance stability of adjustments to the calibration relationship, any suitable approach can be used to inhibit over-correction of the calibration relationship, such as basing adjustments to the calibration relationship on any suitable number of pulses of the power adjust laser pulses.

Figure 2:
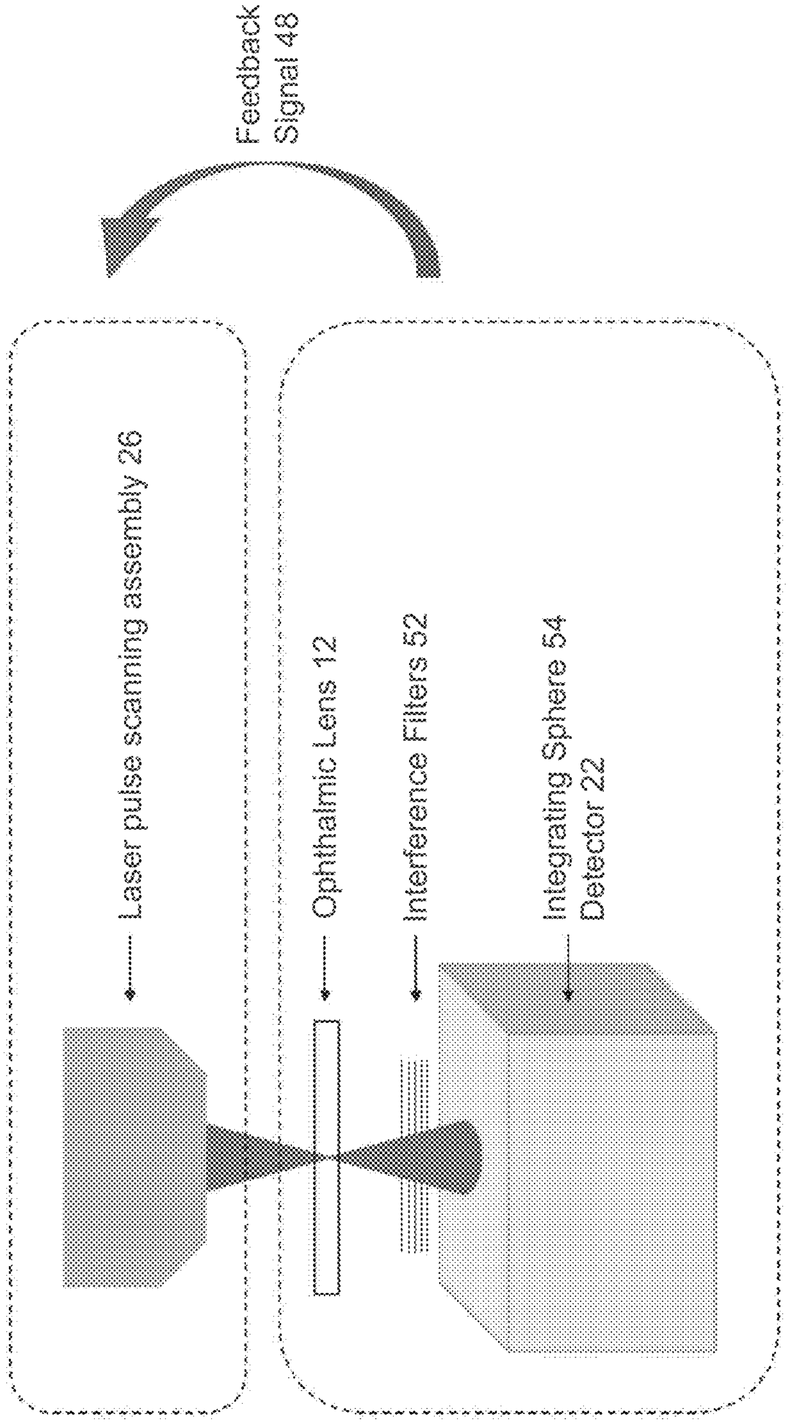
FIG. 2 is a simplified schematic illustration of an approach for generating a feedback signal that can be employed in the system of FIG. 1.

The detector 22 can be integrated into the system 10 in any suitable manner. For example, FIG. 2 is a simplified schematic illustration of a detection assembly 50 that includes an interference filter assembly 52, an integrating sphere 54 and the detector 22. In the illustrated embodiment, the detection assembly 50 is disposed downstream (relative to direction of propagation of the laser pulses) of the ophthalmic lens 12. The integrating sphere 54 has an opening positioned to receive florescence emitted by the ophthalmic lens 12 in response to the energy absorbed by the ophthalmic lens 12 from the laser pulses focused into the ophthalmic lens 12. The interference filter assembly 52 includes one or more filters configured to transmit wavelengths corresponding to the florescence emitted by the ophthalmic lens 12 and block wavelengths corresponding to the power adjusted laser pulses 30. In the illustrated embodiment, the detection assembly 50 is mounted to the support platform 38 and positioned beneath the ophthalmic lens 12.

In some embodiments, the detector 22 is configured to generate the feedback signal 46 so as to be proportional to the amount of pulse energy (of the power adjusted laser pulses 30) that was not absorbed by the ophthalmic lens 12. In such embodiments, the interference filter assembly 52 can include one or more filters configured to transmit wavelengths corresponding to the power adjusted laser pulses 30 and block other wavelengths not corresponding to the power adjusted laser pulses 30. The controller 14 can be configured to indirectly determine the amount of pulse energy absorbed by the ophthalmic lens 12 by processing the feedback signal 46 to measure the amount of pulse energy not absorbed by the ophthalmic lens 12, and then subtracting the amount of pulse energy not absorbed from the pulse energy of the corresponding power adjusted laser pulse 30.

Figure 3:
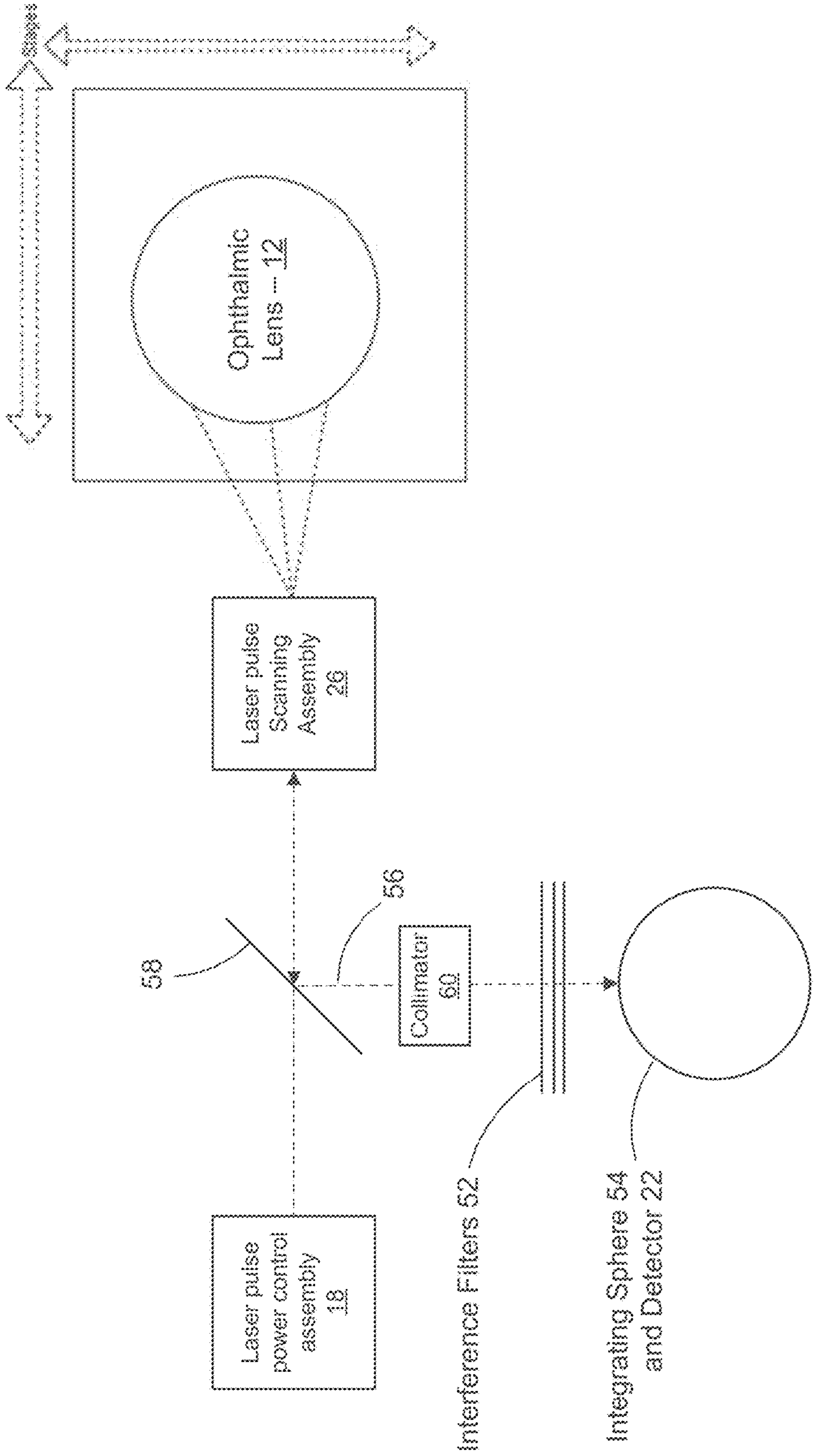
FIG. 3 is a simplified schematic illustration of another approach for generating a feedback signal that can be employed in the system of FIG. 1.

In another embodiment partially illustrated in FIG. 3, the detection assembly 50 is integrated into the system 10 upstream of the laser pulse scanning assembly 26 to measure laser pulse induced florescence 56 that travels back through the laser pulse scanning assembly 26 subsequent to the arrival of a laser pulse at its corresponding focal position in the ophthalmic lens 12. In the illustrated embodiment, the system 10 includes a dichroic mirror 58 positioned upstream (relative to direction of propagation of the power adjusted laser pulses 30) of the laser pulse scanning assembly 26. The dichroic mirror 58 can be configured to reflect wavelengths corresponding to the florescence emitted by the ophthalmic lens 12 in response to the incidence of the focused laser pulse and transmit the power adjusted laser pulses 30. The opening of the integrating sphere 54 can be positioned to receive the florescence reflected by the dichroic mirror. The detection assembly 50 can include a collimator 60 that collimates the florescence 56 prior to the detector 22.

The detection assembly 50 can be integrated into the system 10 in any suitable position and orientation relative to the laser pulse scanning assembly 26 so that the opening of the integrating sphere 54 has a suitable position and orientation to receive the florescence emitted by the ophthalmic lens 12. For example, the detection assembly 50 can be positioned adjacent to the laser pulse scanning assembly 26 with the opening of the integrating sphere suitably oriented orientation to receive the florescence emitted by the ophthalmic lens 12.

The detection assembly 50 can have any suitable configuration. For example, the integrating sphere 54 and/or the interference filters 52 can be omitted from the detection assembly 50.

Figure 4:
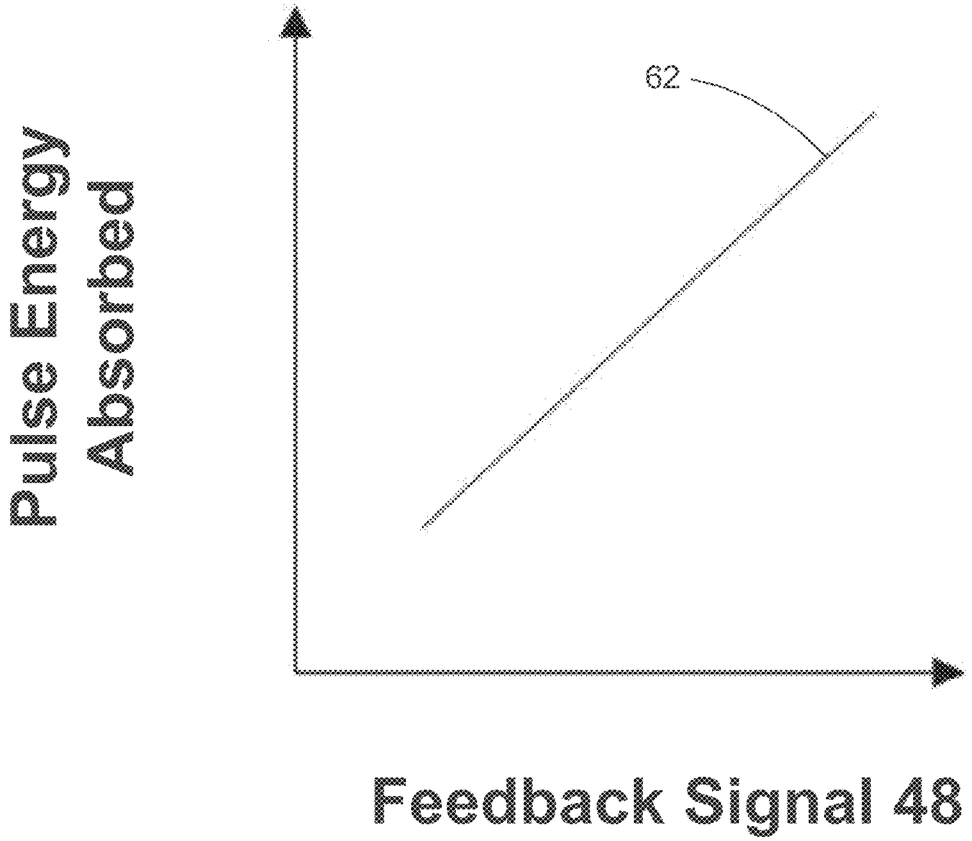
FIG. 4 graphically illustrates an example relationship between a feedback signal and pulse energy absorbed by an ophthalmic lens for use in controlling laser beam pulse power in the system of FIG. 1.

FIG. 4 graphically illustrates an example relationship 62 between a magnitude of the feedback signal 48 (generated by detecting the florescence emitted by the ophthalmic lens 12) and the amount of pulse energy absorbed by the ophthalmic lens 12 by a laser pulse that produced the feedback signal 48. Increasing the power of the power adjusted laser pulses 30 increases the amount of energy absorbed by the ophthalmic lens 12, thereby inducing increased magnitude of emitted florescence, which increases the magnitude of the feedback signal 48. Alternatively, the feedback signal 48 can be generated by detecting the unabsorbed pulse energy and processed as discussed above to determine the amount of pulse energy absorbed by the ophthalmic lens 12 for use in fine-tuning the power of subsequent power adjusted laser pulses 30.

Figure 5:
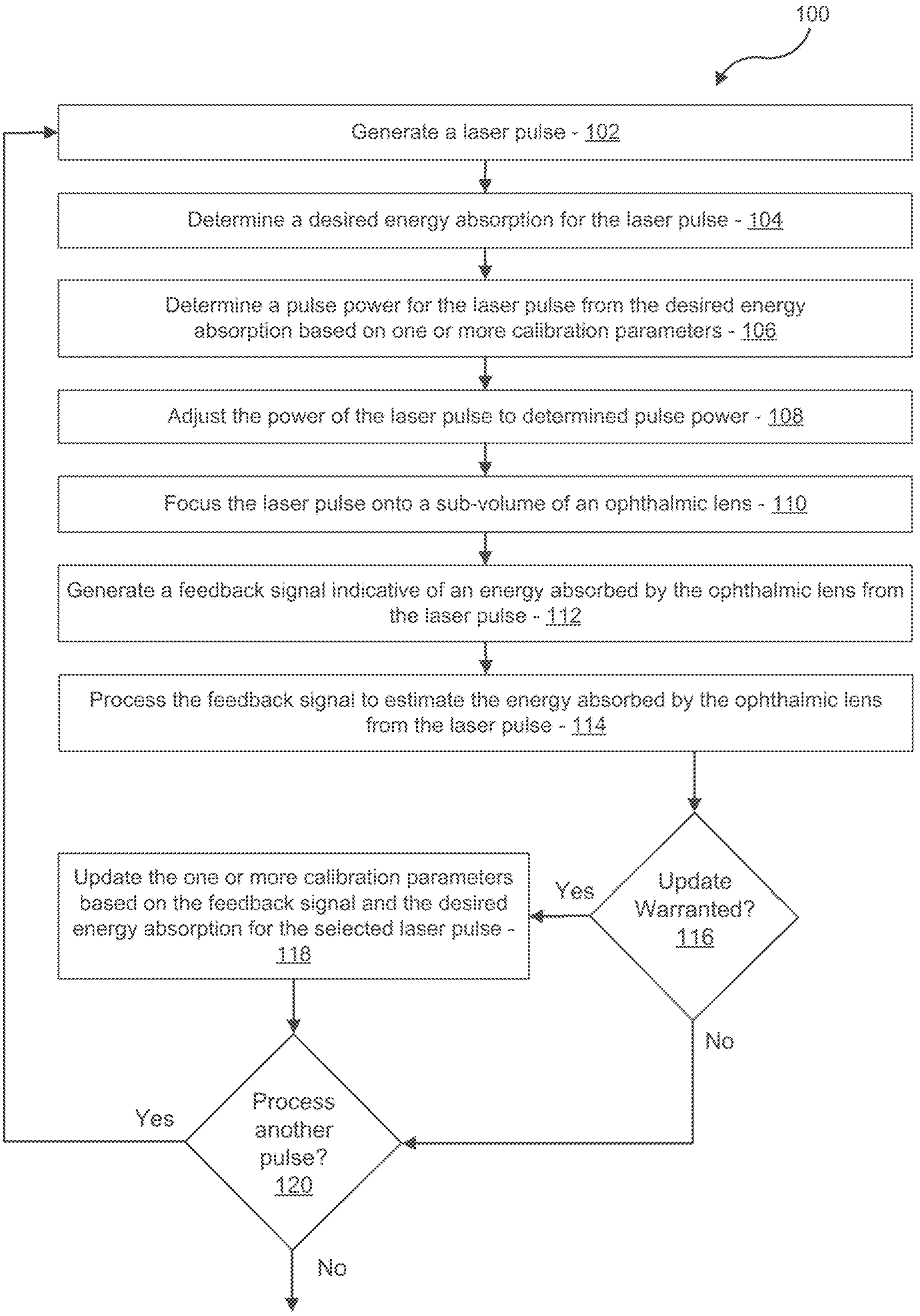
FIG. 5 is a simplified block diagram of a method of calibrating one or more laser pulse power calibration parameters used to determine pulse power for laser pulses from designated energy absorption amounts for the laser pulses, in accordance with embodiments.

FIG. 5 is a simplified block diagram of a method 100 of adjusting one or more laser pulse power calibration parameters used to determine pulse power from desired energy absorption for a sequence of laser pulses used to form subsurface optical structures in an ophthalmic lens, in accordance with embodiments. While the method 100 can be employed in the system 10 as described below, the method 100 can be employed in connection with any suitable system for forming subsurface optical structures in an ophthalmic lens.

In many embodiments, the method 100 comprises a sequence of acts that can be repeatedly performed to repeatedly adjust the one or more laser pulse power calibration parameters. In the following description, the acts of the method 100 are described in connection with a laser pulse of a sequence of laser pulses used to form subsurface optical structures in an ophthalmic lens. The acts of the method 100, however, can be practiced in connection with any suitable sub-sequence of the sequence of laser pulses.

In act 102, a laser pulse (of a sequence of laser pulses used to form subsurface optical structures in an ophthalmic lens) is generated. For example, in the system 10, the laser pulse source 20 generates the sequence of laser pulses 28 having a suitable pulse power, suitable pulse duration, and suitable pulse frequency as described herein. Any suitable laser pulse of the sequence of laser pulses 28 can be designated as the laser pulse.

In act 104, a desired energy absorption for the laser pulse is determined. In many embodiments, a desired energy absorption for each laser pulse of the sequence of laser pulses is predefined for the subsurface optical structures to be formed via the sequence of laser pulses. For example, in the system 10, the scan control data 38 received by the controller 14 includes desired absorbed pulse energies 42 that define a respective desired absorbed pulse energy for each laser pulse of the sequence of laser pulses.

In act 106, a pulse power for the laser pulse is determined from the desired energy absorption for the laser pulse based on one or more calibration parameters. In many embodiments, the one or more calibration parameters are adjusted based on comparing measured pulse energy absorption to desired pulse energy absorption for the laser pulse. Accordingly, the one or more calibration parameters employed in act 106 can be currently applicable one or more calibration parameters, which can have been previously adjusted or can be as initially defined (e.g., by the initial calibration data 44 received by the controller 14 in the system 10). The one or more calibration parameters can define the pulse power for the laser pulse as a function of any suitable parameter of the laser pulse such as, for example, the material of the ophthalmic lens 12, the depth of the focal position of the laser pulse within the ophthalmic lens 12, an X-axis location of the focal position of the laser pulse within the ophthalmic lens 12, a Y-axis location of the focal position of the laser pulse within the ophthalmic lens 12, and/or any suitable combination or sub-combination of the foregoing example parameters of the laser pulse.

In act 108, the power of the laser pulse is adjusted to the pulse power determined for the laser pulse in act 106. Any suitable approach can be used to adjust the power of the laser pulse to the determined pulse power. For example, in the system 10, the controller 14 controls the laser pulse power control assembly 18 so that the power of the laser pulse 28 is adjusted so as to be emitted from the laser pulse power control assembly 18 as a corresponding power adjusted laser pulse 30 having the pulse power determined for the laser pulse in act 106.

In act 110, the laser pulse is focused onto a corresponding focal position in an ophthalmic lens so as to induce a change in refractive index of a sub-volume of the ophthalmic lens to form a portion of the subsurface optical structures. For example, in the system 10, the power adjusted laser pulse 30 is focused by the laser pulse scanning assembly 26 onto a corresponding pre-defined sub-volume of the ophthalmic lens 12, which is positioned at a predefined position relative to the laser pulse scanning assembly 26 by the translation stage assembly 24.

In act 112, a feedback signal is generated that is indicative of the amount of energy absorbed by the ophthalmic lens from the laser pulse. For example, in the system 10, the detector 22 generates the feedback signal 46 in response to radiation incident on the detector 22 that is indicative of the amount of energy absorbed by the ophthalmic lens 12 from the power adjusted laser pulse 30. As described herein, in some embodiments of the system 10, the radiation incident on the detector 22 includes a florescence emitted by the ophthalmic lens 12 in response to the incidence of the power adjusted laser pulse 30 on the corresponding sub-volume of the ophthalmic lens 12. In some embodiments of the system 10, the radiation incident on the detector 22 includes radiation from the power adjusted laser pulse 30 that is not absorbed by the ophthalmic lens 12.

In act 114, the feedback signal is processed to estimate the energy absorbed by the ophthalmic lens from the laser pulse. In many embodiments, the feedback signal is generated throughout the scanning of the sequence of laser pulses and a time segment of the feedback signal corresponding to the laser pulse is processed to determine a signal strength of the feedback signal for the time segment. The energy absorbed by the ophthalmic lens from the laser pulse can be estimated based on the signal strength for the time segment. For example, in the system 10, the controller 14 can store a look-up data table that includes a suitable range of matched values pairs of feedback signal strength magnitude and corresponding estimated pulse energy absorption amount. For a feedback signal strength magnitude falling between signal strength magnitude data values in the look-up data table, the controller 14 can calculate the estimated pulse energy absorption amount using interpolation between the adjacent estimated pulse energy absorption amounts in the look-up data table.

In act 116, the estimated pulse energy absorption amount for the laser pulse is compared with the desired energy absorption for the laser pulse (determined in act 104) to determine if an update to the one or more calibration parameters is warranted. Any suitable criteria can be used to determine if an update to the one or more calibration parameters is warranted. For example, if the estimated pulse energy absorption amount for the laser pulse differs from the desired energy absorption for the laser pulse by more than an acceptable amount, the method 100 can proceed to act 118. If the estimated pulse energy absorption amount for the laser pulse does not differ from the desired energy absorption for the laser pulse by more than an acceptable amount, the method 100 can proceed to act 120.

In act 118, the one or more calibration parameters are updated based on the estimated amount of energy absorbed by the ophthalmic lens from the laser pulse and the desired energy absorption for the laser pulse. For example, the one or more calibration parameters can be updated based on an update factor equal to the desired energy absorption determined in act 104 divided by the estimated amount of energy absorption determined in act 114. To inhibit over correction during the update of the one or more calibration parameters, the one or more calibration parameters can be adjusted by an amount less than indicated by the update factor. In some embodiments, a counter can be used to keep track of the number of laser pulses for which the estimated amount of energy absorption differs from the desired energy absorption and used to trigger an update of the one or more calibration parameters when the counter exceeds a criteria number of pulses so as to inhibit updating the calibration parameters based on a single laser pulse.

In act 120, a determination is made whether to process the feedback signal for another laser pulse. If the answer is yes, the method 100 begins another iteration back at act 102. If the answer is no, the method 100 ends.

Subsurface Optical Structures

Figure 6:
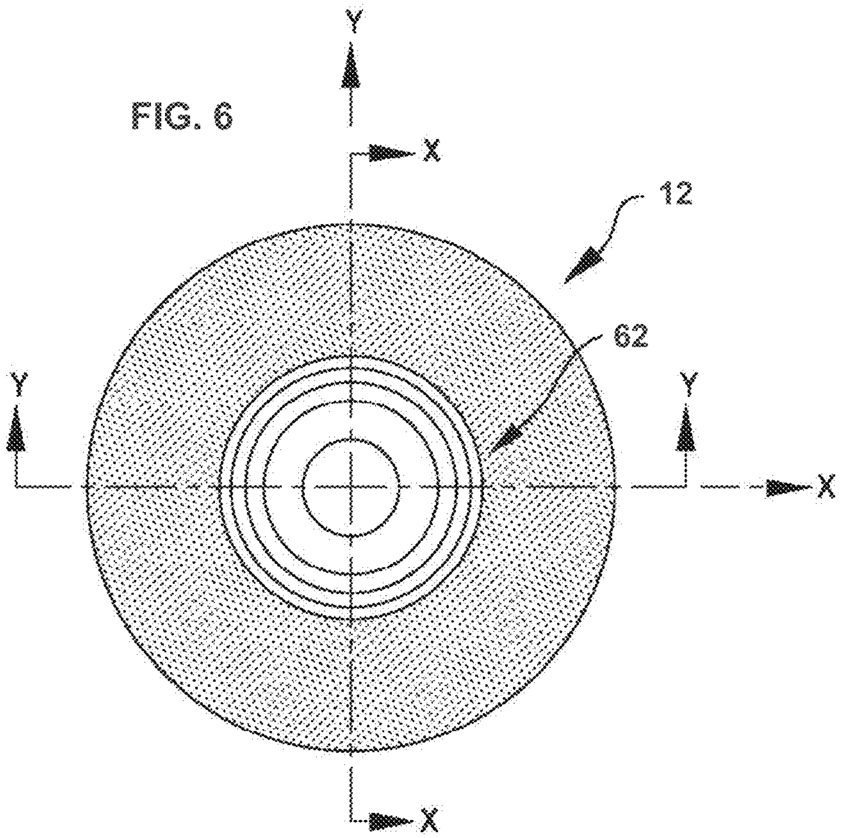
FIG. 6 is a plan view illustration of an ophthalmic lens that includes subsurface optical structures, in accordance with embodiments.

FIG. 6 is a plan view illustration of an ophthalmic lens 12 that includes subsurface optical structures 62 with a distribution of refractive index variations, in accordance with embodiments. The subsurface structures 62 described herein can be formed in any suitable type of ophthalmic lens including, but not limited to, intra-ocular lenses, contact lenses, corneas, spectacle lenses, and native lenses (e.g., a human native lens). The subsurface optical structures 62 are formed of refractive index variation configured to provide a suitable refractive correction for optical aberrations such as astigmatism, myopia, hyperopia, spherical aberrations, coma and trefoil, as well as any suitable combination thereof.

Figure 7:
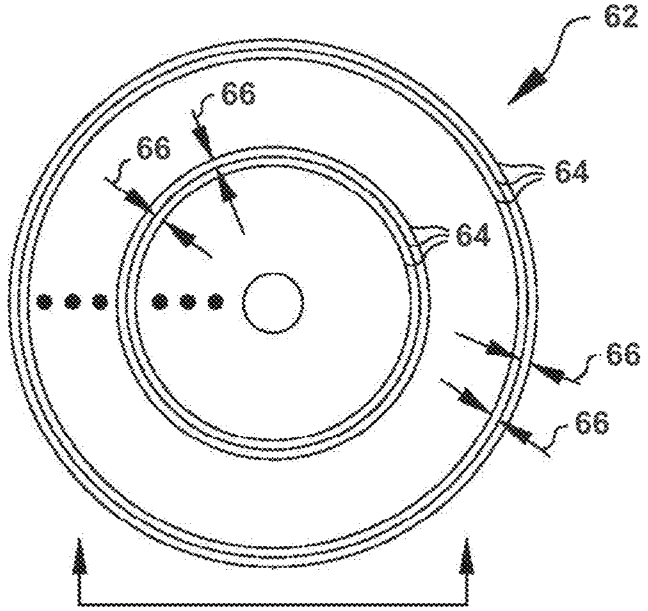
FIG. 7 is a plan view illustration of a layer of the subsurface optical structures of the ophthalmic lens of FIG. 6.

FIG. 7 is a plan view illustration of subsurface optical structures 62 of the ophthalmic lens 12. The illustrated subsurface optical structures 62 includes concentric circular sub-structures 64 separated by intervening line spaces or gaps 66. In FIG. 7, the size of the intervening line spaces 66 is shown much larger than in many actual embodiments. For example, example embodiments described herein have an outer diameter of the concentric circular sub-structures 64 of 3.75 mm and intervening line spaces 66 of 0.25 um, thereby having 7,500 of the concentric circular sub-structures 64 in embodiments where the concentric circular substructures 64 extend to the center of the subsurface optical structure 62. Each of the concentric circular sub-structures 64 can be formed by focusing suitable laser pulses onto sub-volumes of the ophthalmic lens 12 so as to induce changes in refractive index of the sub-volumes so that each of the sub-volumes has a respective refractive index different from an adjacent portion of the ophthalmic lens 12 that surrounds the sub-structure 64 and is not part of any of the subsurface optical structures 12.

In many embodiments, a refractive index change is defined for each sub-volume of the ophthalmic lens 12 that form the subsurface optical structures 62 so that the resulting subsurface optical structures 62 would provide a desired optical correction when formed within the ophthalmic lens 12. The defined refractive index changes are then used to determine parameters (e.g., laser pulse power (mW), laser pulse width (fs)) of laser pulses that are focused onto the respective sub-volumes to induce the desired refractive index changes in the sub-volumes of the ophthalmic lens 12.

While the sub-structures 64 of the subsurface optical structures 62 have a circular shape in the illustrated embodiment, the sub-structures 64 can have any suitable shape and distribution and have a distribution of refractive index variations. For example, a single sub-structure 64 having an overlapping spiral shape can be employed. In general, one or more substructures 64 having any suitable shapes can be distributed with intervening spaces so as to provide a desired diffraction of light incident on the subsurface optical structure 62.

Figure 8:
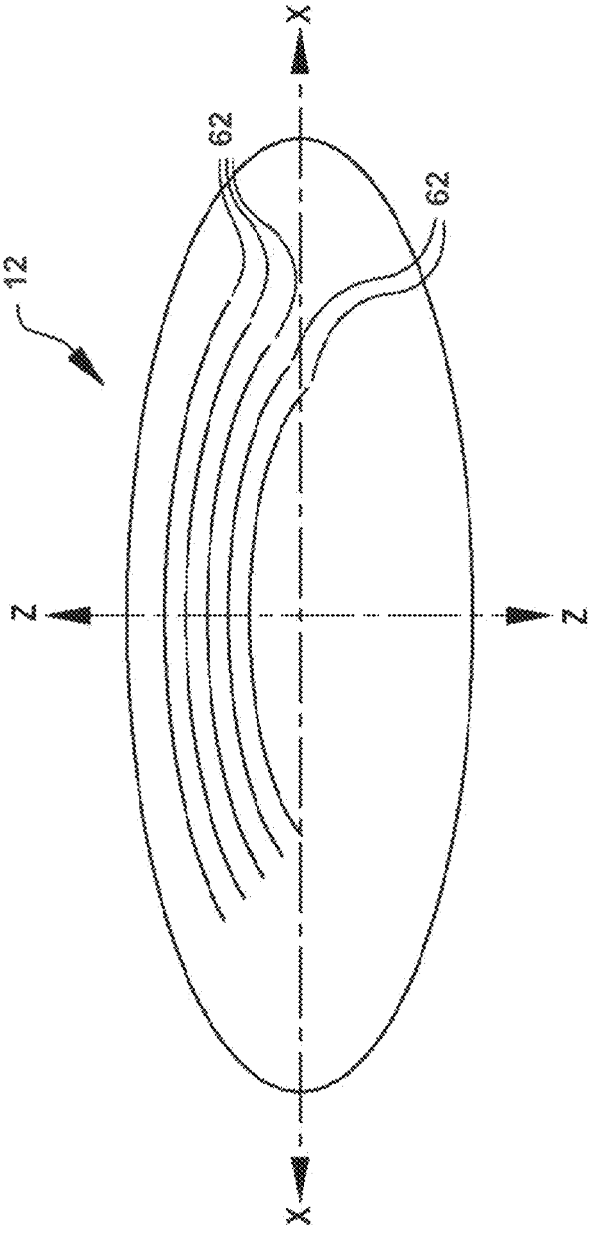
FIG. 8 is a cross-sectional view of the ophthalmic lens of FIG. 6.

FIG. 8 illustrates an embodiment in which the subsurface optical structures 62 are stacked in layers that are separated by intervening layer spaces. In the illustrated embodiment, the subsurface optical structures have a distribution of refractive index variation. The subsurface optical structures 62 can be formed using any suitable scanning approach. For example, the subsurface optical structures 62 can be formed using a scanning approach in which each layer (which comprises one of the subsurface optical structures 62) is sequentially formed starting with the bottom layer and working upward. For each layer, a raster scanning approach can be used to sequentially scan the focal position of the laser pulses along planes of constant X-dimension while varying the Y-dimension and the Z-dimension so that the resulting subsurface optical structures 62 have the curved cross-sectional shapes shown in FIG. 8, which shows an X-direction cross-sectional view of the ophthalmic lens 12. In the raster scanning approach, the laser pulses can be controlled (e.g., via pulse power level and/or selective blocking of laser pulses) to direct laser pulses onto targeted sub-volumes of the ophthalmic lens 12 and not direct laser pulses onto non-targeted sub-volumes of the ophthalmic lens 12, which include sub-volumes of the ophthalmic lens 12 that do not form any of the subsurface optical structures 62, such as the intervening line spaces 66 and the intervening spaces between adjacent layers of the subsurface optical structures 62.

Example 1 is a system for forming subsurface optical structures within an ophthalmic lens. The example 1 system includes a laser pulse source, a laser pulse power control assembly, a scanning assembly, a detector, and a control unit. The laser pulse source is operable to generate a sequence of laser pulses. The laser pulse power control assembly is operable to selectively control an energy of respective laser pulses of the sequence of laser pulses. The scanning assembly is controllable to focus the sequence of laser pulses onto sub-volumes of the ophthalmic lens. The detector is configured to generate a feedback signal indicative of an energy absorbed by the ophthalmic lens from a first laser pulse of the sequence of laser pulses. The control unit is operatively coupled with the laser pulse power control assembly and the detector. The control unit is configured to control operation of the laser pulse power control assembly to selectively control an energy of a second laser pulse of the sequence of laser pulses based on a selected energy of the second laser pulse, a selected energy of the first laser pulse and the feedback signal.

Example 2 is the system of example 1 (or of any subsequent examples individually or in combination), wherein the feedback signal is indicative of a first fluorescence emitted by the ophthalmic lens in response to the energy absorbed from the first laser pulse.

Example 3 is the system of example 2 (or of any other preceding or subsequent examples individually or in combination), further comprising one or more optical filters configured to block a wavelength of light of the first laser pulse from reaching the detector and transmit wavelengths of light of the first fluorescence so that the wavelengths of light of the first fluorescence reach the detector.

Example 4 is the system of example 2 (or of any other preceding or subsequent examples individually or in combination), further comprising an integrating sphere configured to diffuse the first fluorescence prior to the first fluorescence reaching the detector.

Example 5 is the system of example 2 (or of any other preceding or subsequent examples individually or in combination), wherein the first fluorescence propagates back through at least part of the scanning assembly prior to reaching the detector.

Example 6 is the system of example 5 (or of any other preceding or subsequent examples individually or in combination), further comprising a reflector that reflects a portion of the first fluorescence so as to propagate back through the at least part of the scanning assembly prior to reaching the detector.

Example 7 is the system of example 2 (or of any other preceding or subsequent examples individually or in combination), further comprising optical components that collimates the first fluorescence prior to reaching the detector.

Example 8 is the system of any one of examples 1 through 7 (or of any other subsequent examples individually or in combination), wherein the feedback signal is indicative of an energy of a transmitted portion of the first laser pulse, wherein the transmitted portion of the first laser pulse is not absorbed by the ophthalmic lens.

Example 9 is the system of example 8 (or of any other subsequent examples individually or in combination), further comprising an integrating sphere configured to diffuse the transmitted portion of the first laser pulse prior to the transmitted portion of the first laser pulse reaching the detector.

Example 10 is the system of example 8 (or of any other subsequent examples individually or in combination), further comprising a reflector that reflects a portion of the transmitted portion of the first laser pulse so as to propagate back through at least part of the scanning assembly prior to reaching the detector.

Example 11 is the system of example 8 (or of any other subsequent examples individually or in combination), further comprising optical components that collimates the transmitted portion of the first laser pulse prior to reaching the detector.

Example 12 is the system of any one of examples 1 through 7 (or of any other subsequent examples individually or in combination), further comprising one or more positioning stages controlled by the control unit to reposition the detector relative to the ophthalmic lens during formation of the subsurface optical structures within the ophthalmic lens.

Example 13 is the system of any one of examples 1 through 7 (or of any other subsequent examples individually or in combination), further comprising one or more positioning stages controlled by the control unit to reposition the ophthalmic lens and the detector relative to the scanning assembly during formation of the subsurface optical structures within the ophthalmic lens.

Example 14 is the system of any one of examples 1 through 7 (or of any other subsequent examples individually or in combination), wherein the detector comprises an imaging device configured to image a two-dimensional area sized to accommodate a two-dimensional scanning area over which the sequence of laser pulses are scanned onto the ophthalmic lens during formation of the subsurface optical structures within the ophthalmic lens.

Example 15 is the system of any one of examples 1 through 7 (or of any other subsequent examples individually or in combination), wherein the detector comprises a photometer.

Example 16 is the system of any one of examples 1 through 7 (or of any other subsequent examples individually or in combination), wherein the laser pulse power control assembly comprises an acousto-optic modulator.

Example 17 is the system of any one of examples 1 through 7 (or of any other subsequent examples individually or in combination), wherein the ophthalmic lens comprises a contact lens.

Example 18 is the system of any one of examples 1 through 7 (or of any other subsequent examples individually or in combination), wherein the ophthalmic lens comprises an in vivo natural lens of a subject.

Example 19 is the system of any one of examples 1 through 7 (or of any other subsequent examples individually or in combination), wherein the ophthalmic lens comprises an implanted intraocular lens.

Example 20 is the system of any one of examples 1 through 7 (or of any other subsequent examples individually or in combination), wherein the ophthalmic lens comprises a cornea of a subject.

Example 21 is a method of calibrating one or more laser pulse power calibration parameters used to determine pulse power for laser pulses from designated energy absorption amounts for the laser pulses. The example 1 method includes: (a) generating a laser pulse used to produce a power-adjusted laser pulse, (b) determining an adjusted pulse power for the power-adjusted laser pulse from a designated energy absorption by an ophthalmic lens for the power-adjusted laser pulse based on one or more laser pulse power calibration parameters, (c) adjusting power of the laser pulse to produce the power-adjusted laser pulse, wherein the power-adjusted laser pulse has the adjusted pulse power, (d) focusing the power-adjusted laser pulse onto a sub-volume of the ophthalmic lens, (e) generating a feedback signal, by a detector, indicative of an energy absorbed by the ophthalmic lens from the power-adjusted laser pulse, and (f) updating the one or more calibration parameters based on the feedback signal and the designated energy absorption by the ophthalmic lens for the power-adjusted laser pulse.

Example 22 is the method of example 21 (or of any subsequent examples individually or in combination), wherein the feedback signal is indicative of a fluorescence emitted by the ophthalmic lens in response to the energy absorbed by the ophthalmic lens from the power-adjusted laser pulse.

Example 23 is the method of example 22 (or of any other preceding or subsequent examples individually or in combination), further comprising blocking a wavelength of light of the power-adjusted laser pulse from reaching the detector and transmitting a wavelength of light of the fluorescence so that the wavelength of light of the fluorescence reaches the detector.

Example 24 is the method of example 22 (or of any other preceding or subsequent examples individually or in combination), further comprising diffusing the fluorescence prior to the fluorescence reaching the detector.

Example 25 is the method of example 22 (or of any other preceding or subsequent examples individually or in combination), further comprising propagating the fluorescence back through at least part of a scanning assembly prior to reaching the detector, wherein the scanning assembly is used to focus the power-adjusted laser pulse onto the sub-volume of the ophthalmic lens.

Example 26 is the method of example 25 (or of any other preceding or subsequent examples individually or in combination), further comprising reflecting a portion of the fluorescence so as to propagate back through the at least part of the scanning assembly prior to reaching the detector.

Example 27 is the method of example 22 (or of any other preceding or subsequent examples individually or in combination), further comprising collimating the fluorescence prior to reaching the detector.

Example 28 is the method of any one of examples 21 through 27 (or of any other subsequent examples individually or in combination), wherein the feedback signal is indicative of an energy of a transmitted portion of the power-adjusted laser pulse and the transmitted portion of the power-adjusted laser pulse is not absorbed by the ophthalmic lens.

Example 29 is the method of example 28 (or of any other preceding or subsequent examples individually or in combination), further comprising diffusing the transmitted portion of the power-adjusted laser pulse prior to the transmitted portion reaching the detector.

Example 30 is the method of example 28 (or of any other preceding or subsequent examples individually or in combination), further comprising reflecting a portion of the transmitted portion of the power adjusted laser pulse so as to propagate back through a laser pulse scanning assembly prior to reaching the detector.

Example 31 is the method of example 28 (or of any other preceding or subsequent examples individually or in combination), further comprising collimating the transmitted portion of the power adjusted laser pulse prior to reaching the detector.

Example 32 is the method of any one of examples 21 through 27 (or of any other subsequent examples individually or in combination), further comprising repositioning the detector relative to the ophthalmic lens in coordination with scanning of a sequence of power adjusted laser pulses during formation of subsurface optical structures within the ophthalmic lens.

Example 33 is the method of any one of examples 21 through 27 (or of any other subsequent examples individually or in combination), further comprising repositioning the ophthalmic lens and the detector relative to a laser pulse scanning assembly in coordination with scanning of a sequence of power adjusted laser pulses during formation of subsurface optical structures within the ophthalmic lens, wherein the sequence of power adjusted laser pulses is focused into the ophthalmic lens by the laser pulse scanning assembly.

Example 34 is the method of any one of examples 21 through 27 (or of any other subsequent examples individually or in combination), wherein the detector comprises an imaging device configured to image a two-dimensional area sized to accommodate a two-dimensional scanning area over which a sequence of power adjusted laser pulses are scanned into the ophthalmic lens during formation of subsurface optical structures within the ophthalmic lens.

Example 35 is the method of any one of examples 21 through 27 (or of any other subsequent examples individually or in combination), wherein the detector comprises a photometer.

Example 36 is the method of any one of examples 21 through 27 (or of any other subsequent examples individually or in combination), wherein adjusting the power of the laser pulse to produce the power-adjusted laser pulse comprises transmitting the laser pulse through an acousto-optic modulator.

Example 37 is the method of any one of examples 21 through 27 (or of any other subsequent examples individually or in combination), wherein the ophthalmic lens comprises a contact lens.

Example 38 is the method of any one of examples 21 through 27 (or of any other subsequent examples individually or in combination), wherein the ophthalmic lens comprises an in vivo natural lens of a subject.

Example 39 is the method of any one of examples 21 through 27 (or of any other subsequent examples individually or in combination), wherein the ophthalmic lens comprises an implanted intraocular lens.

Example 40 is the method of any one of examples 21 through 27 (or of any other subsequent examples individually or in combination), wherein the ophthalmic lens comprises a cornea of a subject.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for forming subsurface optical structures within an ophthalmic lens, the system comprising:

a laser pulse source operable to generate a sequence of laser pulses;

a laser pulse power control assembly operable to selectively control an energy of respective laser pulses of the sequence of laser pulses;

a scanning assembly controllable to focus the sequence of laser pulses onto sub-volumes of the ophthalmic lens;

a detector configured to generate a feedback signal indicative of an energy absorbed by the ophthalmic lens from a first laser pulse of the sequence of laser pulses; and a control unit operatively coupled with the laser pulse power control assembly and the detector, wherein the control unit is configured to control operation of the laser pulse power control assembly to selectively control an energy of a second laser pulse of the sequence of laser pulses based on a selected energy of the second laser pulse, a selected energy of the first laser pulse and the feedback signal.

2. The system of claim 1, wherein the feedback signal is indicative of a first fluorescence emitted by the ophthalmic lens in response to the energy absorbed from the first laser pulse.

3. The system of claim 2, further comprising one or more optical filters configured to:

block a wavelength of light of the first laser pulse from reaching the detector; and transmit wavelengths of light of the first fluorescence so that the wavelengths of light of the first fluorescence reach the detector.

4. The system of claim 2, further comprising an integrating sphere configured to diffuse the first fluorescence prior to the first fluorescence reaching the detector.

5. The system of claim 2, wherein the first fluorescence propagates back through at least part of the scanning assembly prior to reaching the detector.

6. The system of claim 5, further comprising a reflector that reflects a portion of the first fluorescence so as to propagate back through the at least part of the scanning assembly prior to reaching the detector.

7. The system of claim 2, further comprising optical components that collimates the first fluorescence prior to reaching the detector.

8. The system of claim 1, wherein the feedback signal is indicative of an energy of a transmitted portion of the first laser pulse, wherein the transmitted portion of the first laser pulse is not absorbed by the ophthalmic lens.

9. The system of claim 8, further comprising an integrating sphere configured to diffuse the transmitted portion of the first laser pulse prior to the transmitted portion of the first laser pulse reaching the detector.

10. The system of claim 8, further comprising a reflector that reflects a portion of the transmitted portion of the first laser pulse so as to propagate back through at least part of the scanning assembly prior to reaching the detector.

11. The system of claim 8, further comprising optical components that collimates the transmitted portion of the first laser pulse prior to reaching the detector.

12. The system of claim 1, further comprising one or more positioning stages controlled by the control unit to reposition the detector relative to the ophthalmic lens during formation of the subsurface optical structures within the ophthalmic lens.

13. The system of claim 1, further comprising one or more positioning stages controlled by the control unit to reposition the ophthalmic lens and the detector relative to the scanning assembly during formation of the subsurface optical structures within the ophthalmic lens.

14. The system of claim 1, wherein the detector comprises an imaging device configured to image a two-dimensional area sized to accommodate a two-dimensional scanning area over which the sequence of laser pulses are scanned onto the ophthalmic lens during formation of the subsurface optical structures within the ophthalmic lens.

15. The system of claim 1, wherein the detector comprises a photometer.

16. The system of claim 1, wherein the laser pulse power control assembly comprises an acousto-optic modulator.

17. The system of claim 1, wherein the ophthalmic lens comprises a contact lens.

18. The system of claim 1, wherein the ophthalmic lens comprises an in vivo natural lens of a subject.

19. The system of claim 1, wherein the ophthalmic lens comprises an implanted intraocular lens.

20. The system of claim 1, wherein the ophthalmic lens comprises a cornea of a subject.

* * * * *